US012672900B2

(12) United States Patent
Lasswell et al.

(10) Patent No.: US 12,672,900 B2
(45) Date of Patent: Jul. 7, 2026

(54) SPINAL IMPLANT WITH BALL AND SOCKET JOINT HAVING MULTIPLE RADIUS TEAR SHAPED GEOMETRY

(71) Applicant: Spinal Simplicity, LLC, Overland Park, KS (US)

(72) Inventors: Timothy L. Lasswell, Burlington (CA); Parham Rasoulinejad, London (CA); John B. Medley, Fergus (CA)

(73) Assignee: Spinal Simplicity, LLC, Overland Park, KS (US)

( * ) Notice: Subject to any disclaimer, the term of this patent is extended or adjusted under 35 U.S.C. 154(b) by 418 days.

(21) Appl. No.: 18/221,054

(22) Filed: Jul. 12, 2023

(65) Prior Publication Data

US 2023/0355281 A1 Nov. 9, 2023

Related U.S. Application Data

(63) Continuation of application No. 16/821,525, filed on Mar. 17, 2020, now Pat. No. 11,737,792, which is a continuation of application No. 16/010,626, filed on Jun. 18, 2018, now Pat. No. 10,624,678.

(60) Provisional application No. 62/645,520, filed on Mar. 20, 2018, provisional application No. 62/522,452, filed on Jun. 20, 2017.

(51) Int. Cl.
| | |
|---|---|
| *A61B 17/70* | (2006.01) |
| *A61F 2/44* | (2006.01) |
| *A61F 2/46* | (2006.01) |
| *A61B 90/00* | (2016.01) |

(Continued)

(52) U.S. Cl.
CPC ...... *A61B 17/7047* (2013.01); *A61B 17/7001* (2013.01); *A61B 17/7005* (2013.01); *A61B 17/7043* (2013.01); *A61B 17/7076* (2013.01); *A61F 2/4455* (2013.01); *A61F 2/4611* (2013.01); *A61B 17/7082* (2013.01); *A61B 2090/031* (2016.02); *A61F 2002/2835* (2013.01); *A61F 2002/30322* (2013.01); *A61F 2002/30538* (2013.01); *A61F 2002/30622* (2013.01); *A61F 2002/30784* (2013.01); *A61F 2002/30841* (2013.01)

(58) Field of Classification Search
CPC ............ A61B 17/7001; A61B 17/7005; A61B 17/7043; A61B 17/7047; A61B 17/7076; A61F 2/4455; A61F 2/4611
See application file for complete search history.

(56) References Cited

U.S. PATENT DOCUMENTS

| | | | | |
|---|---|---|---|---|
| 4,611,582 A | * | 9/1986 | Duff ................... | A61B 17/7007 606/260 |
| 2011/0178552 A1 | * | 7/2011 | Biscup ............... | A61B 17/7047 606/246 |

(Continued)

*Primary Examiner* — Nicholas J Plionis
(74) *Attorney, Agent, or Firm* — Erise IP, P.A.

(57) ABSTRACT

A spinal fusion clamp implant that connects two vertebra, preferably the C1 and C2 vertebra. The clamp implant includes a clamp assembly that connects to the C1 vertebra. The clamp assembly includes at least one superior jaw and at least one inferior jaw. The superior jaw and the inferior jaw are opposedly arranged and clamp onto posterior arch of the C1 vertebra. The clamp implant also includes an implant assembly that connects to the implant used in C2, and a connection system that connects the clamp assembly with said C2 implant assembly.

20 Claims, 10 Drawing Sheets

(51)  Int. Cl.
    *A61F 2/28*             (2006.01)
    *A61F 2/30*             (2006.01)

(56)            References Cited

U.S. PATENT DOCUMENTS

2013/0144386 A1\*   6/2013   Horton ................ A61B 17/707
                                           623/17.11
2018/0008321 A1\*   1/2018   Stern ................ A61B 17/7043

\* cited by examiner

Type II Fracture

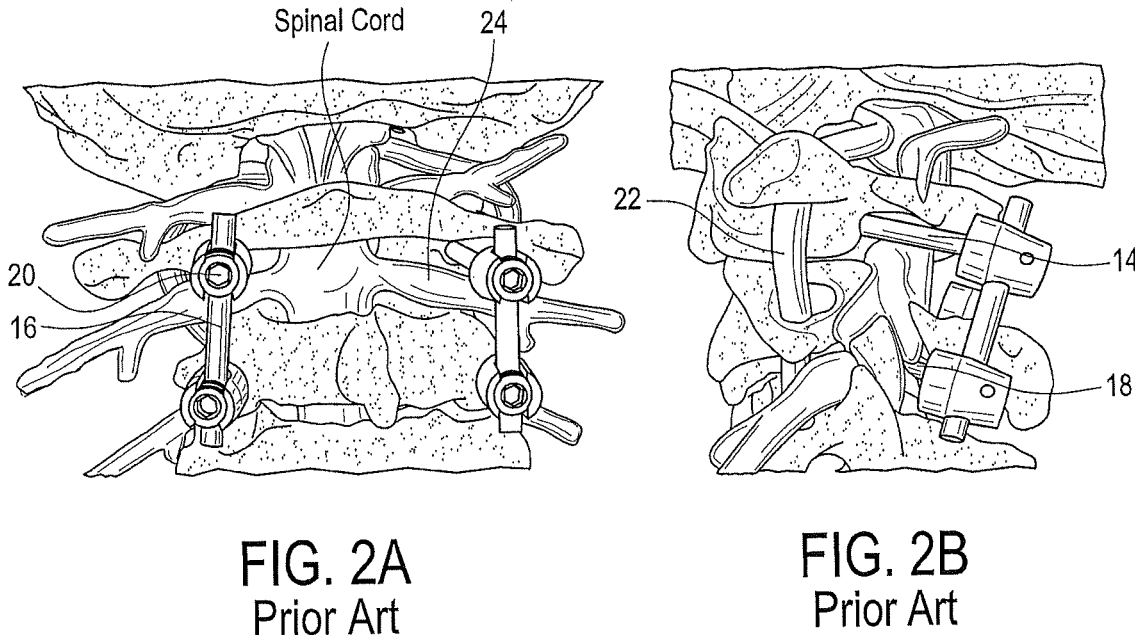
FIG. 2A
Prior Art
FIG. 2B
Prior Art
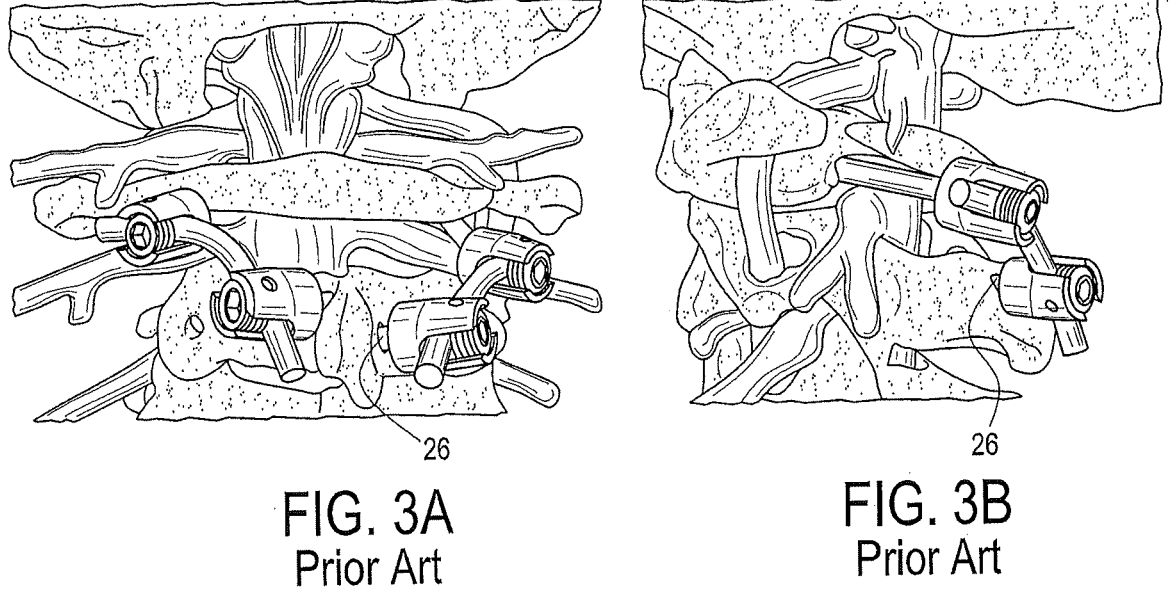
FIG. 3A
Prior Art
FIG. 3B
Prior Art

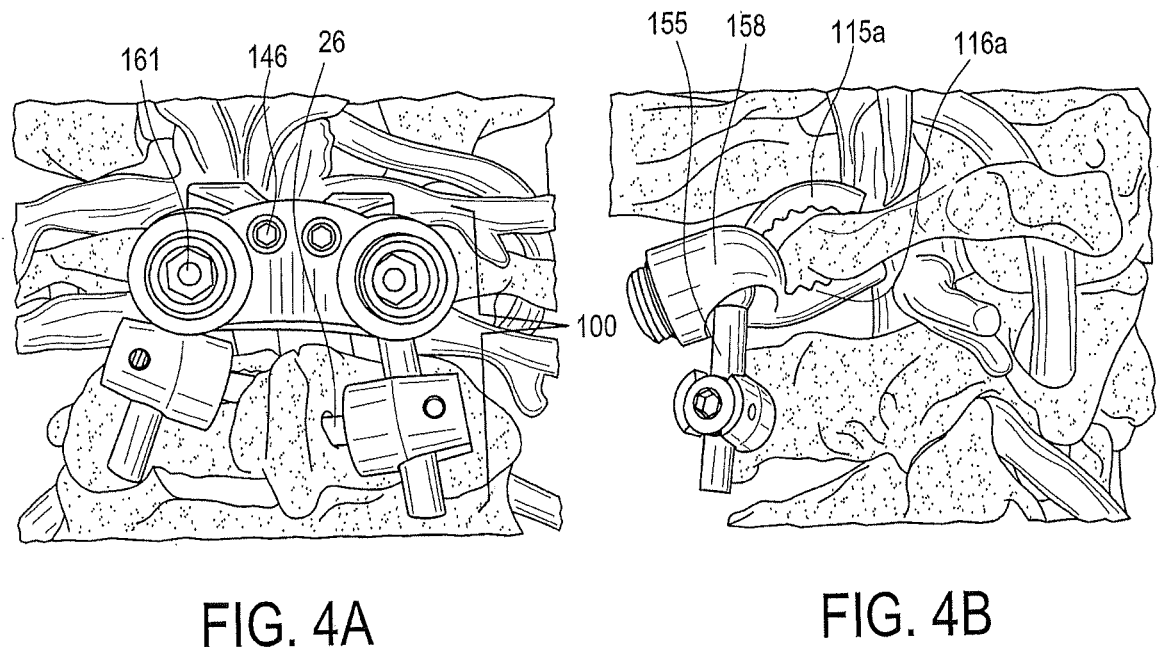
FIG. 4A
FIG. 4B
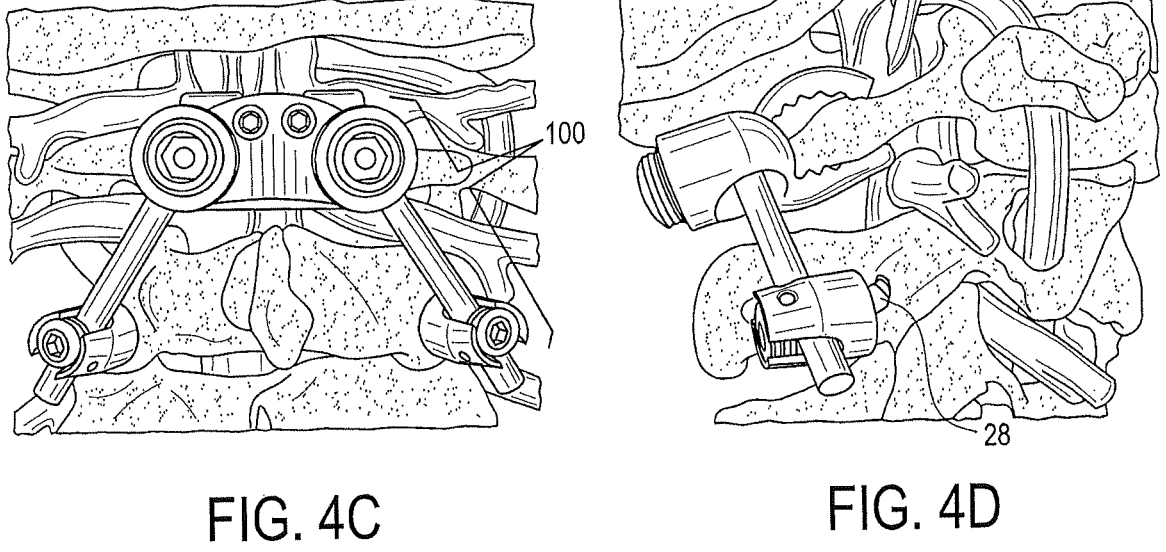
FIG. 4C
FIG. 4D

SPINAL IMPLANT WITH BALL AND SOCKET JOINT HAVING MULTIPLE RADIUS TEAR SHAPED GEOMETRY

CROSS REFERENCE TO RELATED APPLICATIONS

This application is a continuation application of U.S. patent application Ser. No. 16/821,525 filed Mar. 17, 2020, which is a continuation of Ser. No. 16/010,626 filed Jun. 18, 2018, now U.S. Pat. No. 10,624,678 issued Apr. 21, 2020, which claims priority from U.S. Provisional Application No. 62/522,452, filed on Jun. 20, 2017, and U.S. Provisional Application No. 62/645,520, filed on Mar. 20, 2018, the disclosures of which are hereby incorporated herein by reference in their entireties.

FIELD OF THE INVENTION

The present invention relates to the field of spinal fusion fixation devices. More particularly, the invention relates to a spinal fusion clamp implant that connects a first vertebra (e.g., the C1 vertebra) with a second vertebra (e.g., the C2 vertebra).

BACKGROUND OF THE INVENTION

The first and second cervical spine vertebrae (C1 and C2) are unique due to the presence of a synovial "pin joint" (referred to as the atlantoaxial joint), compared to the intervertebral discs in the lower cervical spine. As shown in FIG. 1A, the C2 vertebra 2 has a boney structure called the odontoid 4 which acts as the pin that sits within the ring of C1 vertebra 6. The odontoid 4 articulates against the anterior ring of C1 and is held in place by ligamentous structures. Atlantoaxial instability (AAI) occurs when there is excessive motion at the atlantoaxial joint most commonly caused by traumatic fracture of the odontoid. If left untreated, AAI can cause chronic pain, myelopathy and even death when even mild additional trauma is sustained to the destabilized joint segment. Odontoid fractures are classified into three types depending on the location of the fracture line in the C2 vertebra. Type II fractures, such as shown in FIG. 1B, are the most common and due to a higher risk of fracture non-union, surgical treatment is recommended. However, a surgical approach is not always possible, especially in the elderly patient population, due to concerns related to intraoperative blood loss, operating time, surgical invasiveness and recovery time. Given these concerns, only approximately 50% of the current elderly patient population is healthy enough to undergo surgery for AAI. Even when surgical treatment is possible, deciding the optimal treatment is not trivial and a common consensus has not yet been reached in clinical practice.

Posterior spinal fusion, in which an implant construct is used to hold adjacent vertebrae together until they heal into a single piece of solid bone, has become the most common surgical treatment for type II odontoid fractures in elderly patients when surgery is feasible. Since being introduced in 2001, the Harms construct has become the standard fixation for posterior fusion of the atlantoaxial segment due to good construct stability and high fusion rates.

FIGS. 2A and 2B show posterior and lateral views, respectively, of the use of the Harms construct in atlantoaxial fusion on a model of the upper cervical spine. The Harms construct consists of two polyaxial screws 14 that are inserted into the lateral masses 10 of C1, connected by titanium rods 16 to two additional polyaxial screws 18 that are inserted into the pedicles 12 of C2. Cap screws 20 are tightened down on the rods 16 to lock the construct in place and provide immediate stability to the joint until long term fusion occurs. The surgical procedure for implanting the Harms construct is very invasive, requiring a long incision and a dissection all the way down to the C1 lateral masses 10. The blood loss associated with this surgery tends to be very high due to disturbing the capillaries and venous plexus around the vertebral artery 22 and C2 nerve root 24. Additionally, placement of the C1 lateral mass screw 14 is risky due to the potential for injuring the vertebral artery 22 and often the C2 nerve root 24 is sacrificed to get a safer screw trajectory. Due to these surgical concerns, approximately half of the elderly patient population is not fit for surgery and must instead be treated conservatively with hard collar immobilization, ultimately leading to high fracture nonunion rates and a permanent instability.

Attempts have been made both clinically and experimentally to develop new constructs and surgical techniques that better suit the needs of the C1/C2 segment. For example, Huang et al. (Posterior atlantoaxial fixation: a review of all techniques, *The Spine Journal*, Vol. 15, 2015, pp. 2271-2281) discusses, inter alia, various C1-C2 atlantoaxial stabilization/fixation techniques involving screws and clamps or hooks, such as C1-C2 apofix clamps, C1 hook combined with a C2 pedicle screw, and a C1 screw combined with C2 hooks. However, these techniques are not sufficiently stable (e.g., clamp slippage occurs frequently), result in pseudarthrosis, and/or are generally difficult to use in surgery. On the other hand, as shown in the posterior and lateral views of FIGS. 3A and 3B, respectively, and as reported in Dorward and Wright (Seven Years of Experience With C2 Translaminar Screw Fixation: Clinical Series and Review of the Literature, *Neurosurgery*, Vol. 68, No. 6, June 2011, pp. 1491-1499), C2 translaminar screws 26 have been used with excellent clinical success to replace C2 pedicle screws 18 in the Harms construct and thus eliminate the risk of a C2 screw injuring the vertebral artery 22. Although C2 translaminar screws 26 have reduced risk in posterior fusion procedures, the surgery remains equally invasive as the Harms procedure with regard to blood loss and operating time because of the continued use of C1 lateral mass screws 14.

It is therefore desirable to provide a spinal fusion fixation device that does not suffer from the above drawbacks.

Advantages of the present invention will become more fully apparent from the detailed description of the invention below.

SUMMARY OF THE INVENTION

The present invention in the various embodiments described below addresses the problems discussed above and other problems, by providing a spinal fusion clamp implant that connects a first vertebra with a second vertebra. The clamp implant includes a clamp assembly that connects to the first vertebra. The clamp assembly includes a superior jaw assembly having at least one superior jaw, and includes an inferior jaw assembly having at least one inferior jaw. The superior jaw and inferior jaw are opposedly arranged and clamp onto the first vertebra. The clamp implant also includes an implant assembly that connects to the second vertebra, and a connection system that connects the clamp assembly with the implant assembly. In a preferred embodiment, the first vertebra is the C1 vertebra, and the superior jaw and inferior jaw clamp onto the posterior arch of the C1 vertebra.

The present invention advantageously reduces the invasiveness of atlantoaxial posterior fusion surgeries by providing a clamp implant to replace C1 lateral mass screws and instead affix to the posterior arch of C1. Additional embodiments and additional features of embodiments for the clamp implant are described below and are hereby incorporated into this section.

BRIEF DESCRIPTION OF THE DRAWINGS

The features, objects, and advantages of the present disclosure will become more apparent from the detailed description set forth below when taken in conjunction with the drawings in which like reference characters identify correspondingly throughout and wherein:

FIG. 2A is an upper cervical spine anatomical model, posterior view, showing the Harms construct used in atlantoaxial fusion, and FIG. 2B is a lateral view of the same.

FIG. 3A is an upper cervical spine anatomical model, posterior view, showing a fusion construct that uses C2 translaminar screws, and FIG. 3B is a lateral view of the same.

FIG. 4A is a posterior view of the clamp implant of the present invention used with C2 translaminar screws; FIG. 4B is a lateral view of the clamp implant used with C2 translaminar screws; FIG. 4C is a posterior view of the clamp implant used with C2 pedicle screws; and FIG. 4D is a lateral view of the clamp implant used with C2 pedicle screws.

FIG. 9A shows the final fusion construct created with the C1 clamp implant and C2 translaminar screws; FIG. 9B shows the final fusion construct created with the C1 clamp implant and C2 pedicle screws.

DETAILED DESCRIPTION OF THE PREFERRED EMBODIMENTS

Figure 1A:
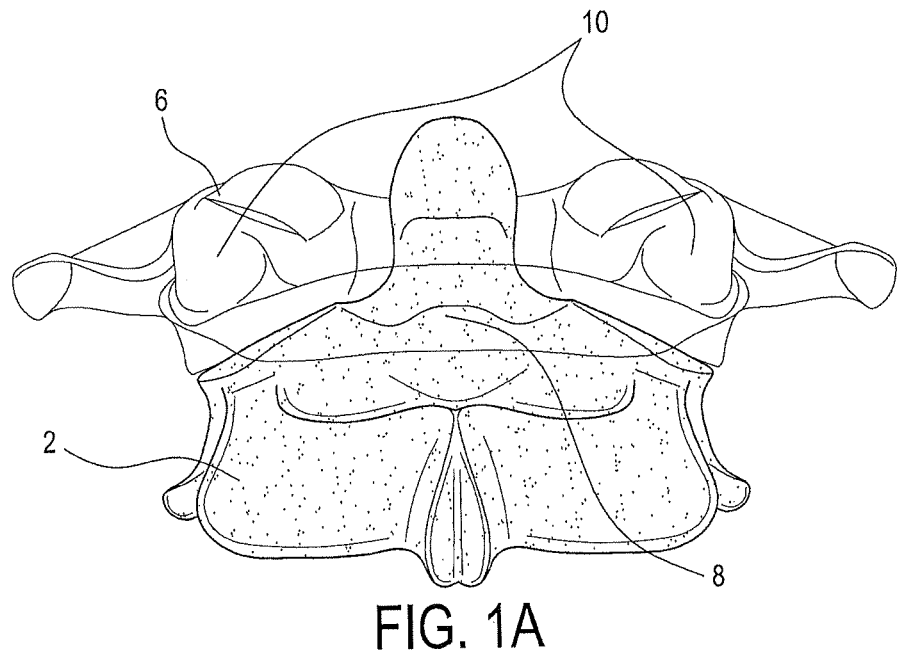
FIG. 1A shows the boney anatomy of the atlantoaxial joint (C1, partially transparent to show odontoid placement)
Figure 1B:
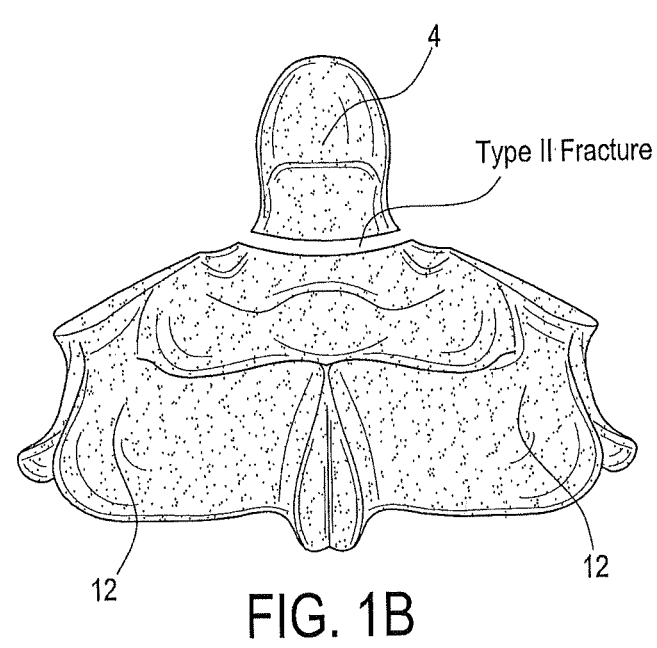
FIG. 1B is a view of the C2 vertebra showing a type II odontoid fracture.

In the following detailed description, reference is made to certain embodiments. This detailed description is merely intended to teach a person of skill in the art further details for practicing preferred aspects of the present teachings and is not intended to limit the scope of the claims. Therefore, combinations of features disclosed in the following detailed description may not be necessary to practice the teachings in the broadest sense, and are instead taught merely to describe particularly representative examples of the present teachings. It is to be understood that other embodiments may be employed and that various structural changes may be made.

With reference to FIGS. 4A-9C, the present invention is directed to a clamp implant 100 configured to connect a first vertebra (preferably the C1 vertebra 6) with a second vertebra (preferably the C2 vertebra 2). The clamp implant 100 comprises: (i) a clamp assembly 110 (FIG. 6A) configured to connect to the C1 vertebra 6, (ii) an implant assembly, such as translaminar screws 26 or pedicle screws 28, to connect to the C2 vertebra 2, and a connection system 150 that connects the clamp assembly 110 with the implant assembly, i.e., translaminar screws 26 or pedicle screws 28.

Clamp assembly 110 comprises a superior jaw assembly 115 of two superior jaws 115a, and an inferior jaw assembly 116 of two inferior jaws 116a. The superior jaws 115a and the inferior jaws 116a are opposedly arranged and are configured to clamp onto the posterior arch 8 of the C1 vertebra 6. The jaws of the clamp are concave in shape to conform to the superior and inferior sides of the C1 posterior arch. The fixation surface of the inferior jaw 116a is designed with less concavity (i.e., greater radius of curvature) than the superior jaw 115a, since the inferior side of the C1 posterior arch is generally flatter than the superior side. In different implant variations, the concavity of the inferior and superior jaws may be the same. Alternatively, the inferior and superior jaws may also be designed to have no concavity (i.e, be flat) or may even be designed to have a variety of convex shapes.

Figures 5A, 5B:
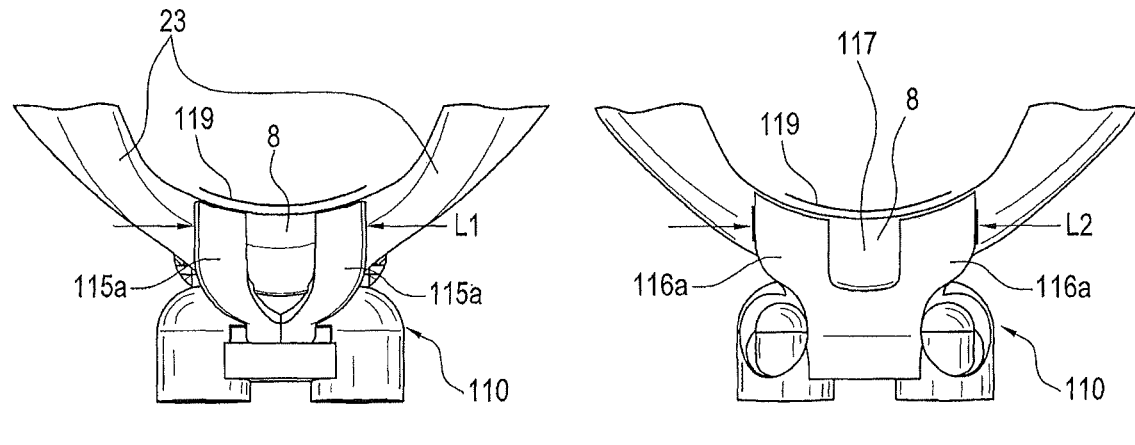
FIGS. 5A and 5B are superior and inferior axial views, respectively, of the clamp implant on the C1 posterior arch (polyaxial rods and rod cap screws omitted).

As shown in FIGS. 5A and 5B, the inferior jaw assembly 116 has a cutout 117 in the midsection which acts as a window for bone graft material to promote long term fusion. The superior jaw assembly 115 has two parts to enhance its grip on the C1 posterior arch 8 that may be slightly non-symmetrical in its anatomical geometry, as described in further detail below. The gap between the two parts of the superior jaw assembly 115 may also act as a window for bone graft material. In an alternative embodiment, the inferior jaws 116a can have no bone graft cutout, creating a single, slightly stiffer, inferior jaw. This single inferior jaw can also be smaller in width to effectively create a three pronged (rather than the current four pronged) clamp that could allow bone graft materially to be placed on the lateral sides of the jaw rather than the medial sides.

To avoid injury to the vertebral artery 22 (which sits atop the vertebral groove 23), the lateral footprint distance $L_1$ of the superior jaws 115a is less than the lateral footprint distance $L_2$ of the inferior jaws 116a. Injury to the vertebral artery 22 is not a concern for the inferior jaws 116a, so the $L_2$ dimension can be larger to provide additional component stiffness which increases overall implant stability. In different implant variations, the $L_1$ and $L_2$ dimensions could vary, and $L_1$ may not be smaller than $L_2$.

As further shown in FIGS. 5A and 5B, respectively, in the axial (horizontal) plane, the clamp jaws are designed to have a curved cutout 119 that follows the C1 posterior arch so that the implant does not protrude into the spinal canal. Optionally, rounded edges can be added to these curved cutouts to further reduce the risk of pointed objects near the spinal canal.

Figure 6A:
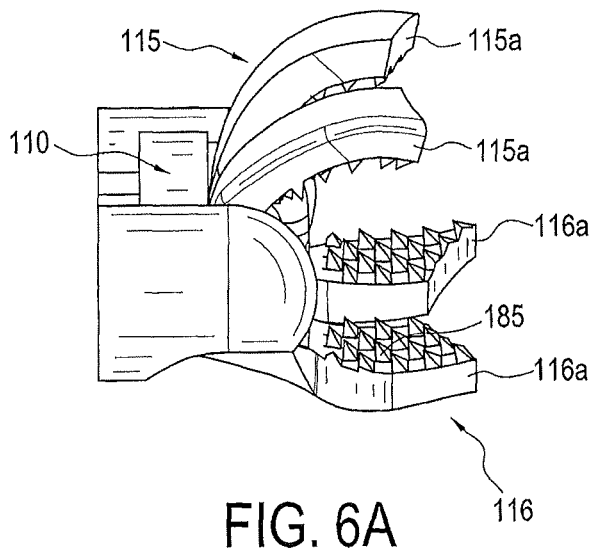
FIG. 6A is a side profile of the clamp implant, showing the saw tooth surface for bone fixation
Figure 6B:
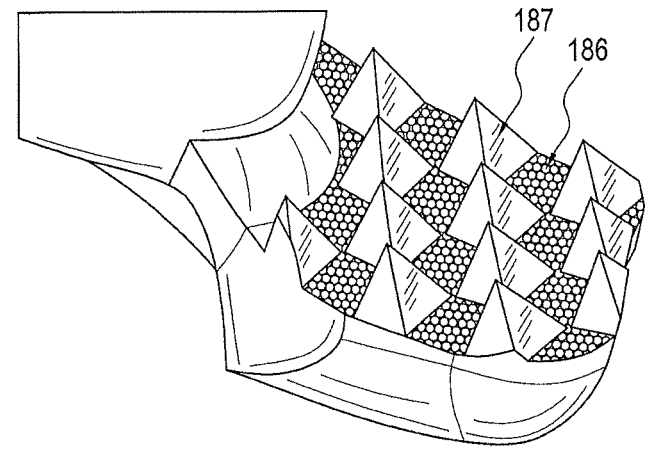
FIG. 6B shows the detail of the spiked teeth of the jaws, and the porous material between the teeth.

As shown in FIG. 6, the superior jaws 115a and the inferior jaws 116a preferably have a saw tooth surface 185. The saw tooth design prevents the implant from backing out in the posterior direction. Movement in the anterior direction is not a concern since the body of the clamp butts up against the C1 posterior arch 8. In different embodiments of this design, the jaw surface may consist of cylindrical spikes, pyramid spikes, a knurled surface or a porous surface. Such surfaces (including the saw tooth surface 185) may produce bone strains that bioactively encourage bone ongrowth/ingrowth. A combination of jaw surfaces may also be used, such as the case shown in FIG. 6B, where porous surface regions 186 are positioned between spike tips 187. The porous surface regions can be created as part of a three dimensional printing method of fabricating the clamp component or by temporarily attaching a metal powder to the surface regions and then sintering it to provide a permanent fused porous surface structure or by using a plasma spraying technique with a metal powder. Additionally, the jaw surface can include a material attached to it (including porous regions) that helps promote bone ongrowth/ingrowth biochemically, such as hydroxyapatite or hydroxyapatite with tricalcium phosphate. All of the above described jaw surfaces help the jaws grip the C1 posterior arch 8 to minimize or eliminate movement (e.g., micromotion) between the jaw surface and bone of the C1 posterior arch from the time of surgery until the bony fusion is established, thus enhancing overall implant stability.

Figure 7D:
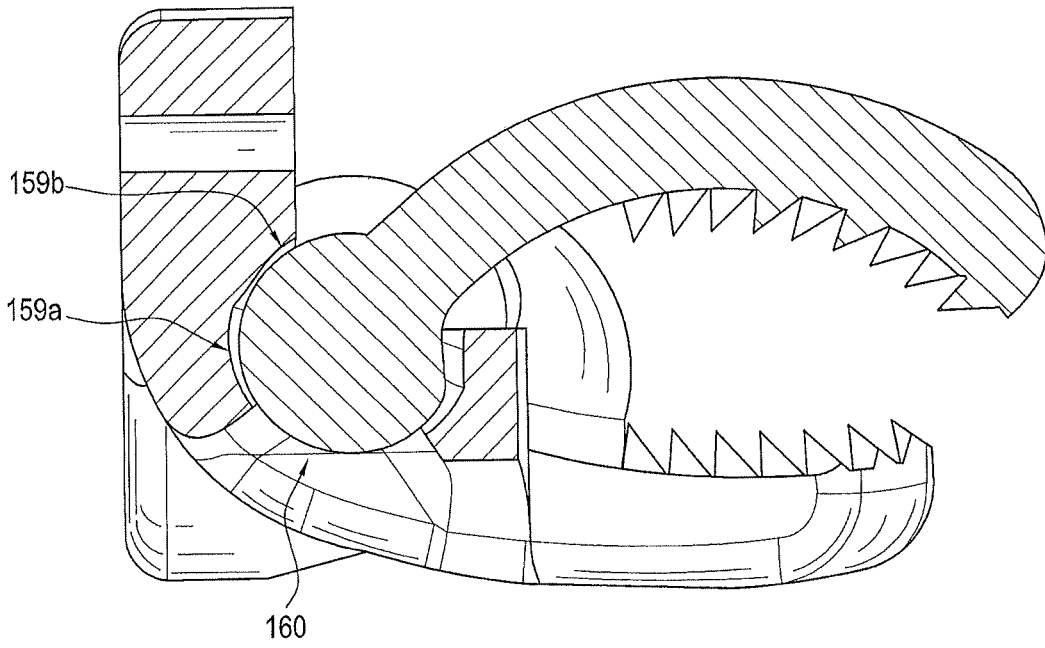
FIG. 7D shows the multiple radius tear drop geometry of the socket, and a cutout in the socket.
Figures 7A, 7B:
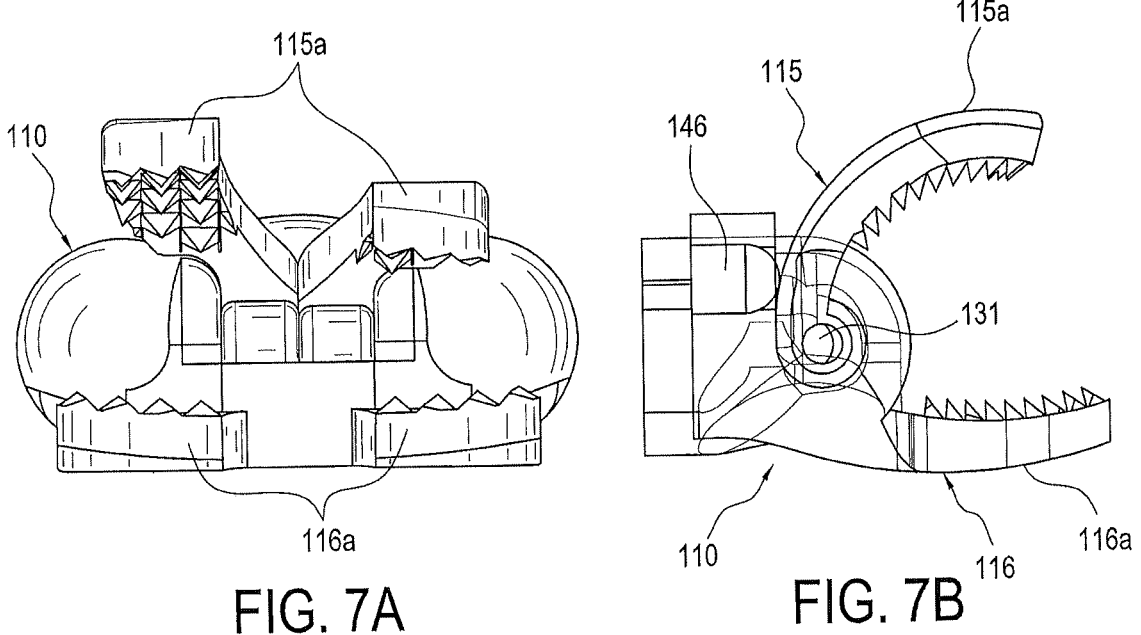
FIG. 7A is an anterior view of the implant showing independent jaw articulation.
FIG. 7B is a side detail of the implant showing the jaw locking mechanism (clamp body and inferior jaw is shown partially transparent)
Figure 7C:
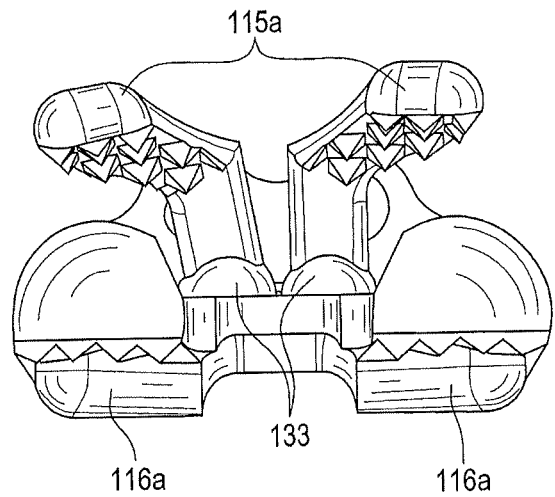
FIG. 7C shows the ball joint geometry to allow additional degrees of freedom for jaw motion.

As shown in the anterior view of FIG. 7A, the two superior jaws 115a are designed to both articulate and be locked independently of each other. This allows the implant to adapt to non-symmetric anatomy and still achieve adequate fixation. To provide articulation, the superior jaw assembly 115 may comprise a (linear) single axial joint 131 (see FIGS. 7A and 7B) associated with each of the superior jaws 115a. The single axial joint 131 allows for single axial movement of the superior jaw 115a with respect to the corresponding inferior jaw 116a. Alternatively, the superior jaw assembly 115 may include a ball joint 133 (see FIG. 7C) associated with each of the superior jaws 115a. Each ball joint 133 allows for multi-axial movement of the associated superior jaw 115a with respect to the corresponding inferior jaw 116a. The ball joint geometry allows for additional degrees of motion and a better fit between the implant and the posterior arch of C1. Additive manufacturing techniques can be used to manufacture this ball joint as a one step process with no assembly required. In this case, relief cut-outs (or windows) 160 may be included in the socket of the ball joint geometry to allow for the escape of un-sintered powder (see FIG. 7D). The socket of the ball joint may also comprise a multiple radius tear drop geometry, with a larger radius 159a and a smaller radius 159b, in order to allow more clearance between the ball and socket during the additive manufacturing process while still allowing a tight clearance when the ball is seated in the locked position. Standard assembly and manufacturing techniques using CNC's, lathes, precision grinding and precision tooling may also be used to create the ball joint.

The superior jaw assembly 115 further includes jaw locking screws 146 (see FIGS. 7B and 8B-8D) that can be tightened to lock the superior jaws 115a in place after the implant has been placed on the C1 posterior arch 8 and fitted to the anatomy. The clamp body has two threaded holes to allow for placement of the jaw locking screws 146. A buttress thread may be used to prevent loosening of the locking screws. As shown in FIG. 7B, the top surface of the jaws that come in contact with the jaw locking screws 146 are designed to act as cam surfaces that provide progressive closing of the jaws as the jaw locking screws 146 are tightened. The ends of the jaw locking screws 146 are rounded to promote a smooth sliding motion as the jaws 115a close. Tightening of the jaw locking screws 146 also controls the clamping pressures at the jaw/bone fixation interfaces. In other embodiments of this design, the jaw locking screws 146 can be in line with the center of rotation of the jaws and simply act as set screws. The clamping pressure of the jaws 115a can then be controlled by external tooling, such as pliers, placed around the jaws. Alternatively, one jaw locking screw (instead of two) could be placed centrally in the body of the clamp to lock both jaws simultaneously.

Alternatively or additionally, in a likewise manner to that described above, the two inferior jaws 116a may be designed so they are capable of independent movement from each other. Thus, the inferior jaw assembly 116 may comprise a (linear) single axial joint (not shown) similar to single axial joint 131 associated with the inferior jaws 116a, or a ball joint (not shown), similar to ball joint 133 associated with the inferior jaws 116a. The inferior jaw assembly 116 would then further comprise jaw locking screws (not shown), similar to jaw locking screws 146, for locking the inferior jaws 116a in place.

As described in further detail below, an implant assembly, such as C2 translaminar screws 26 or pedicle screws 28, is configured to be implanted into translaminar portions or pedicle portions of the C2 vertebra (see FIGS. 4A-4D and 9A-9C).

Figures 8A, 8B:
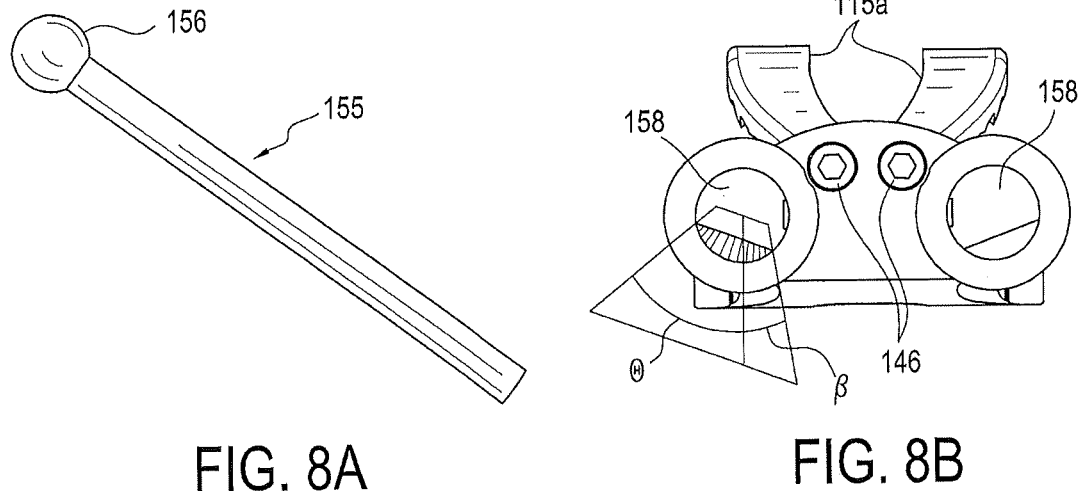
FIG. 8A shows the polyaxial rod of the present invention with a spherical head.
FIG. 8B shows the socket articulation for the polyaxial rod.
Figures 8C, 8D:
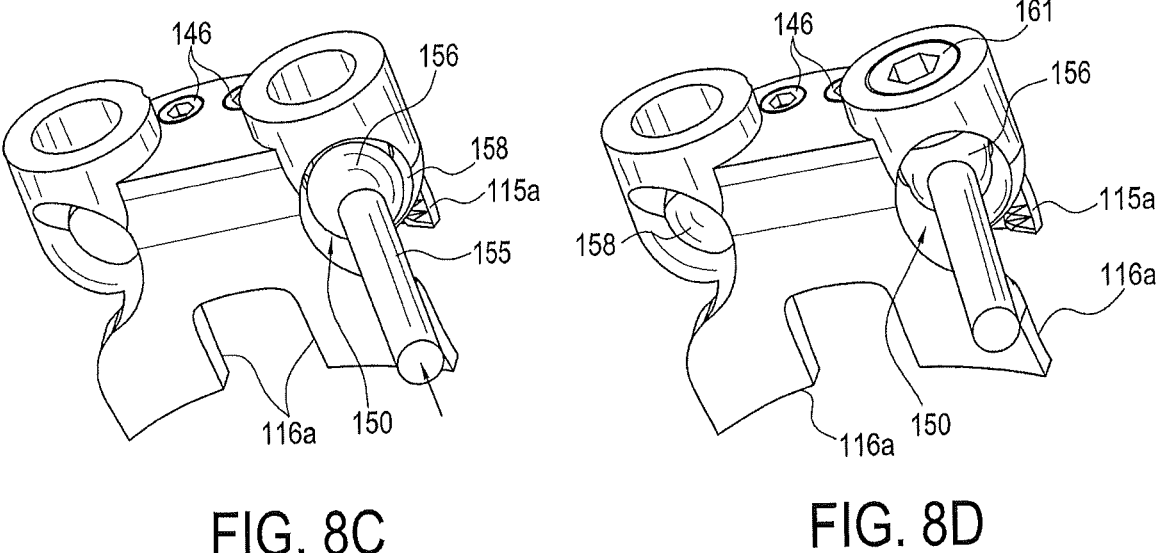
FIG. 8C shows the polyaxial rod insertion into the clamp body.
FIG. 8D shows the locking of the polyaxial rod into the socket by tightening the rod cap screw.

Connection system 150 comprises a polyaxial connection system comprising a polyaxial rod 155 with a spherical head 156, and a rod cap screw 161 configured to be tightened to apply pressure to the spherical head 156, thereby locking the polyaxial rod 155 in place. More specifically, once the clamp 110 has been locked into place on the C1 posterior arch 8, rods 155 are inserted into the clamp to connect the clamp 110 to the implant used in C2, thus creating the overall clamp implant fusion construct. The use of C2 pedicle screws 28 and/or C2 translaminar screws 26 has been previously discussed as feasible implant components that could be used in conjunction with the C1 clamp 110. However, the C1 clamp 110 can be used with any C2 implant component designed to be connected to the C1 implant component through the use of rods. As shown in FIG. 8A, the rods for the C1 clamp (referred to as polyaxial rods 155) have spherical heads so that, prior to tightening of the rod cap screw 161, they can articulate within the polyaxial sockets 158 of the C1 clamp body. The sockets, shown in FIGS. 8C and 8D, are designed to allow ±30° of rod rotation in any direction. Sockets 158 have a bias and allow more rotation in the lateral direction (θ) and less rotation in the medial direction (β), as shown in FIG. 8B, to provide a better fit when pedicle screws are used in C2. As shown in FIG. 7D, sockets 158 can also have additional windows or cutouts 160 and/or holes to improve the aesthetic appearance of the device as well as reduce the overall bulk of the device. The posterior regions of the sockets are threaded to allow for the rod cap screws 161 to be tightened into place. A buttress thread may be used to prevent loosening of the rod cap screws. The polyaxial rods 155 are inserted through the bottom of the clamp body (FIG. 8C) and then slid forward into the sockets when the rod cap screws 161 are threaded into place (FIG. 8D). The rods 155 are specifically designed to be inserted in the bottom of the clamp body so that a fully threaded hoop can be maintained for the rod cap screws. This full hoop minimizes deformation due to the splaying generated during thread tapping and rod cap screw tightening. In another embodiment, slots or cutouts are provided in the sockets to allow the rods to be inserted from the posterior and/or lateral directions.

Once both rods 155 are placed in the sockets 158, they can be connected to the C2 implant assembly, such as C2 translaminar screws 26 (FIG. 9A) or C2 pedicle screws (FIG. 9B). Tightening down all of the rod cap screws 161 then locks the clamp implant into place and creates a stable fusion construct.

Figure 9C:
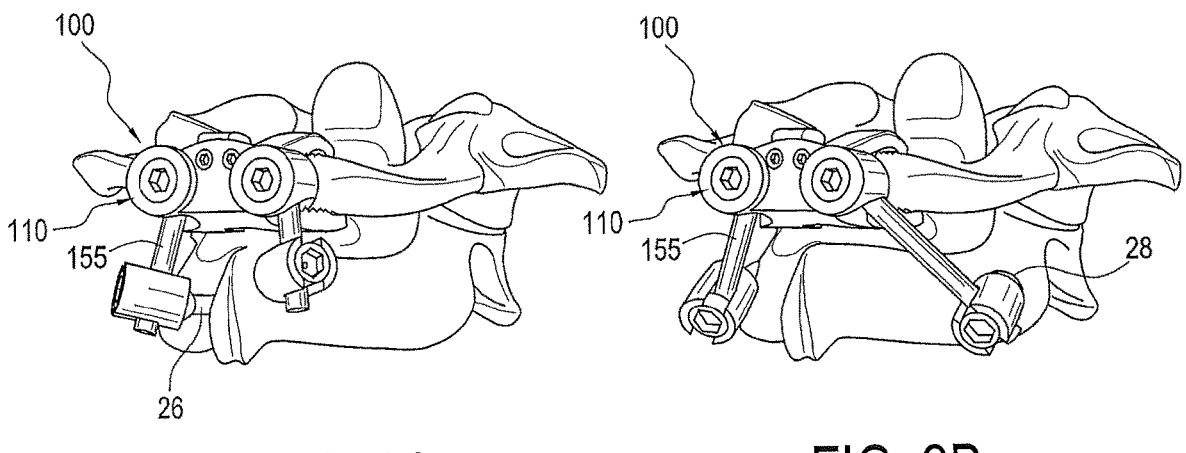
FIG. 9C shows the final fusion construct created with the C1 clamp, C2 pedicle screws and a C0 plate.
Figure 9C:
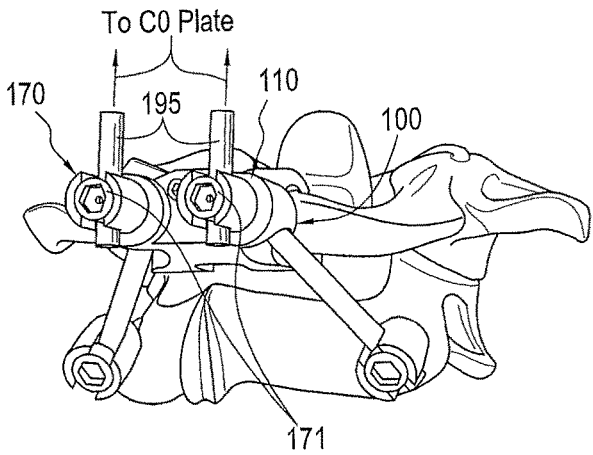

The clamp implant of the present invention can also be modified for a multi-level fusion that includes the occipital (C0) vertebra. In this case, the rod cap screws 161 are replaced with rod cap screws that also have polyaxial fixation heads 170 (FIG. 9C). Standard cervical rods 195 can then be attached to these polyaxial heads 170 (via tightening of polyaxial set screws 171) and connected to a C0 vetebra plate (not shown). Additionally, the construct can be extended below C2 by using longer polyaxial rods. These rods may be non-linear to allow better alignment with the rest of the patient anatomy and/or cervical instrumentation. The extended construct may allow for the implant to be fixed to a vertebra different than (or in addition to) the C2 vertebra (e.g., the C3 vertebra). Fixation of the implant to another vertebra may employ similar or different implantation techniques as those described in this disclosure for the C2 vertebra.

The clamp implant of the present invention is manufactured from a biocompatible material such as pure titanium, titanium alloy, stainless steel or cobalt chromium alloy or a material with potential for bone ongrowth/ingrowth such as porous tantalum. Alternatively, or additionally, porous surfaces with or without coatings such as hydroxyapatite or hydroxyapatite with tricalcium phosphate can be used on parts of the implant to bioactively encourage bone ongrowth/ingrowth. Some parts of the clamp implant of the present invention can also be made from a polymer such as PEEK or a polymer composite such as carbon fiber reinforced PEEK. Ceramic inserts can be used for some of the bearing surfaces.

Figure 10:
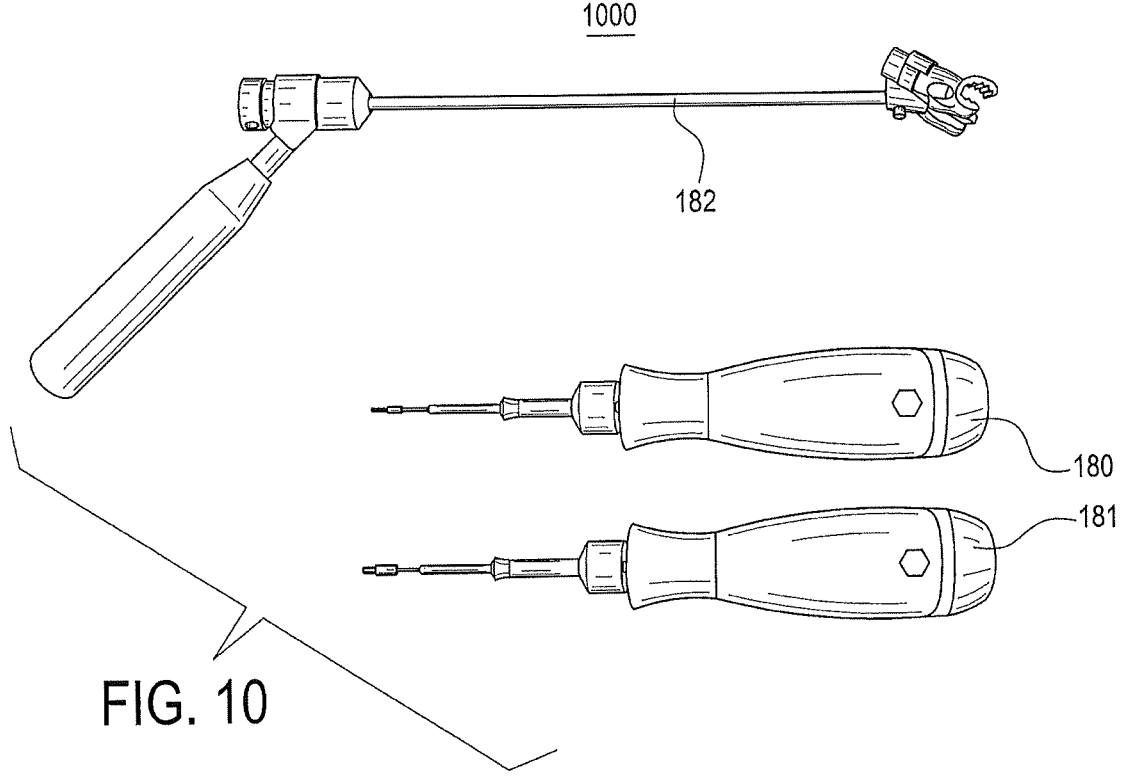
FIG. 10 shows the instrumentation used in conjunction with the implant of the present invention.
Figure 11A:
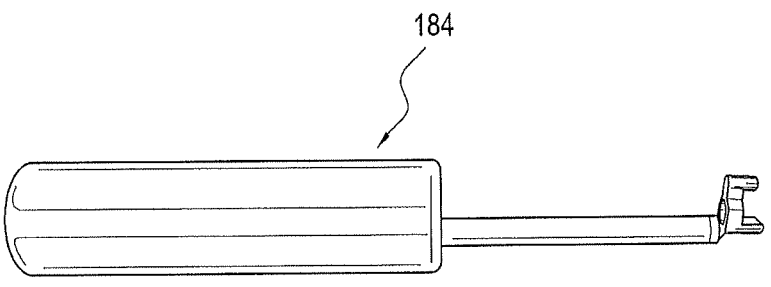
FIG. 11A shows an alternative inserter tool with an axial handle and no angular offset.
Figure 11B:
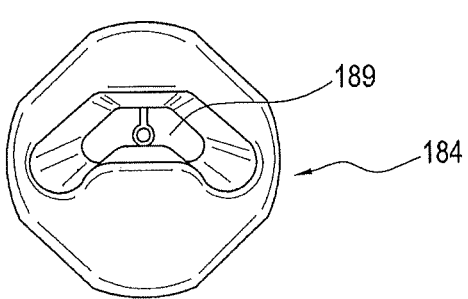
FIG. 11B shows an end view of the alternative inserter tool with a window in the handle for screwdriver access.
Figure 11C:
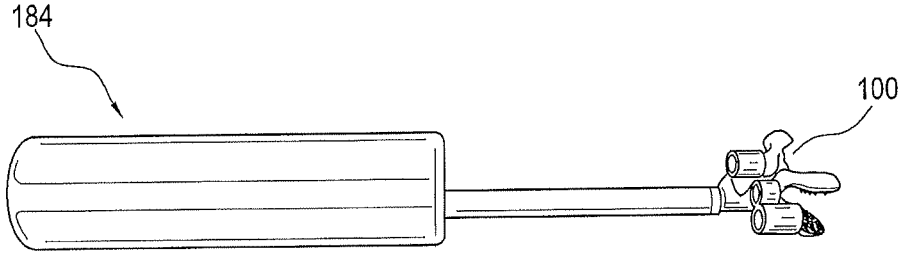
FIG. 11C shows the alternative inserter tool with the clamp implant attached to the distal end of the tool.

The instrumentation 1000 used in conjunction with the implant, shown in FIG. 10, consists of two torque limited screwdrivers 180, 181 and an inserter tool 182. The implant is first placed on the inserter tool through the use of clips, screws, latches or an interference fit. While on the inserter tool, the jaws of the implant may be kept open using clips or latches or through the use of springs and wires that may consist of a Nitinol mechanism. The jaws may also be kept open by a frictional interference fit between the ball and socket geometry 133 previously described. The shaft of the inserter tool can have an angular offset to allow for better visualization of the posterior arch during insertion of the implant. Alternatively, an inserter tool 184 with an axial handle and no angular offset as shown in FIG. 11A may be used. In this case, the handle of the inserter tool will have a plurality of through holes or one larger window 189, shown in FIG. 11B, to allow for the torque screwdrivers to access the locking screws. The inserter tool 182, 184, with clamp implant 100 mounted on the tool (FIG. 11C), is then used to place the implant on the posterior arch of C1 and hold it in place until the jaw locking screws are tightened down. During the tightening of the jaw locking screws, the inserter tool 182, 184 also acts as the counter torque device. Once the jaws are tight, the inserter tool may be used to reduce fractures (if a fracture is present) and/or obtain ideal alignment at the fusion stage before inserting the full construct of the clamp implant. This reduction or fracture alignment is done while the inserter tool is still connected to the implant, allowing the handle of the inserter tool to provide better leverage on re-positioning C1. The inserter tool 182 is then removed to free up space for the remainder of the full construct, i.e., screws 26, 28 to be implanted in C2, and connection system 150. Upon final tightening of the polyaxial rods 155, the inserter tool 182, 184 can once again be used as a counter torque device.

The clamp implant of the present invention can be provided in a variety of sizes to cater to the anatomy of the entire patient population. Three-dimensional printing may be used to fabricate any or all of the components in the manufacture of the clamp implant. Three-dimensional printing may also be used to introduce porosity or a lattice structure to encourage bone ingrowth/ongrowth.

Although embodiments are described above with reference to a clamp implant comprising a clamp assembly that, for example, clamps onto the posterior arch of C1, the jaw assemblies of the clamp assembly described in any of the above embodiments may alternatively clamp onto other portions of C1 or other vertebra. Such alternatives are considered to be within the spirit and scope of the present invention, and may therefore utilize the advantages of the configurations and embodiments described above.

In addition, although embodiments are described above with reference to a clamp implant comprising an implant assembly (e.g., for C2), the implant assembly described in any of the above embodiments may alternatively be replaced with a secondary clamp assembly (e.g., of the types used for C1 described above). The jaw assemblies for this secondary clamp assembly may clamp onto any portion of the C2 or other vertebra. Such alternatives are considered to be within the spirit and scope of the present invention, and may therefore utilize the advantages of the configurations and embodiments described above.

The above description and drawings are only to be considered illustrative of specific embodiments, which achieve the features and advantages described herein. Modifications and substitutions to specific process conditions may be made. Accordingly, the embodiments of the invention are not considered as being limited by the foregoing description and drawings.

More generally, even though the present disclosure and exemplary embodiments are described above with reference to the examples according to the accompanying drawings, it is to be understood that they are not restricted thereto. Rather, it is apparent to those skilled in the art that the disclosed embodiments can be modified in many ways without departing from the scope of the disclosure herein. Moreover, the terms and descriptions used herein are set forth by way of illustration only and are not meant as limitations. Those skilled in the art will recognize that many variations are possible within the spirit and scope of the disclosure as defined in the following claims, and their equivalents, in which all terms are to be understood in their broadest possible sense unless otherwise indicated.

The invention claimed is:

1. A spinal implant for implanting at a spine, the spinal implant comprising:
   a clamp assembly comprising:
   a superior jaw;
   an inferior jaw opposedly positioned to the superior jaw;
   a clamp body defining a ball joint connecting the superior jaw to the inferior jaw,
   wherein the clamp body defines a socket,
   wherein the clamp assembly is configured to clamp a first vertebra;
   an implant assembly configured to fasten to a second vertebra;
   a connection system comprising:
   a rod having a head and an end,
   wherein the socket receives the head of the rod and the end of the rod couples to the implant assembly to connect the clamp assembly with the implant assembly;
   a rod screw positioned proximate the head of the rod and received within the clamp body,
   wherein rotation of the rod screw locks the head of the rod into the socket to stabilize the spinal implant; and
   a locking screw received within the clamp body,
   wherein the locking screw contacts an outer surface of the superior jaw and rotation of the locking screw advances the locking screw along the outer surface of the superior jaw to close the clamp assembly on the first vertebra.

2. The spinal implant of claim 1,
   wherein the head of the rod is spherical, and the rod is configured to articulate polyaxially within the socket prior to rotation of the rod screw to lock the rod into the socket.

3. The spinal implant of claim 1,
   wherein the rod screw threadedly couples to a posterior region of the socket.

4. The spinal implant of claim 3,
   wherein rotation of the rod screw causes the rod screw to advance within the posterior region of the socket,
   wherein rotation of the rod screw causes an end of the rod screw to contact the head of the rod and apply pressure to the head of the rod, thereby locking the rod into the socket.

5. The spinal implant of claim 1, the ball joint comprising:
   a ball fixedly connected to the superior jaw; and
   a ball joint socket having a multiple radius tear drop geometry,
   wherein the ball joint socket receives the ball,
   wherein movement of the ball within the ball joint socket causes the superior jaw to move multi-axially with respect to the inferior jaw.

6. The spinal implant of claim 5,
   wherein the ball joint socket comprises a first curved portion and a second curved portion,
   wherein the first curved portion has a radius greater than a radius of the second curved portion.

7. The spinal implant of claim 1,
   wherein the clamp body comprises an aperture for receiving the locking screw therein,
   wherein the locking screw controls articulation of the clamp assembly.

8. The spinal implant of claim 1,
   wherein the ball joint is manufactured in a one step process using additive manufacturing.

9. The spinal implant of claim 1, wherein the superior jaw comprises a saw tooth surface.

10. A medical implant, the medical implant comprising:
    a clamp assembly comprising:
    a top jaw;
    a bottom jaw opposedly positioned to the top jaw;
    a clamp body defining a ball joint connecting the top jaw to the bottom jaw,
    wherein the clamp body defines a socket,
    an implant assembly;
    a connection system comprising:
    a polyaxial rod having a head and an end,
    wherein the socket receives the head of the polyaxial rod and the end of the polyaxial rod couples to the implant assembly to connect the clamp assembly to the implant assembly;
    a rod screw threadedly coupled to the clamp body,
    wherein rotation of the rod screw locks the head of the polyaxial rod into the socket to stabilize the medical implant; and
    a locking screw received within the clamp body,
    wherein the locking screw contacts an outer surface of the top jaw and rotation of the locking screw advances the locking screw along the outer surface of the top jaw to close the clamp assembly on a first vertebra.

11. The medical implant of claim 10,
    wherein the top jaw and the bottom jaw cooperate together to clamp a first vertebra therebetween, and the implant assembly fastens to a second vertebra.

12. The medical implant of claim 10,
    wherein an end of the locking screw contacts the outer surface of the top jaw,
    wherein the end of the locking screw is rounded in shape to promote a smooth sliding motion when the locking screw advances along the outer surface of the top jaw.

13. The medical implant of claim 10,
    wherein rotation of the rod screw causes an end of the rod screw to contact the head of the polyaxial rod and apply pressure to the head of the polyaxial rod, thereby locking the polyaxial rod into the socket.

14. The medical implant of claim 10,
    wherein a lateral footprint distance of the top jaw is less than a lateral footprint distance of the bottom jaw.

15. The medical implant of claim 10, the ball joint comprising:
    a ball fixedly connected to the top jaw; and
    a ball joint socket having a multiple radius tear drop geometry,
    wherein the ball joint socket receives the ball,
    wherein movement of the ball within the ball joint socket causes the top jaw to move multi-axially with respect to the bottom jaw.

16. The medical implant of claim 10,
    wherein an inner surface of at least one of the top jaw and the bottom jaw comprises a textured surface for gripping bone,
    wherein the textured surface comprises spike tips.

17. The medical implant of claim 16,
    wherein the inner surface of at least one of the top jaw and the bottom jaw further comprises porous surface regions positioned between the spike tips,
    wherein the porous surface regions are configured to promote bone ingrowth.

18. The medical implant of claim 10, wherein the clamp body comprises an aperture for receiving the locking screw therein.

19. A method of performing spinal surgery comprising:
inserting a spinal implant into a patient at a spine, the
spinal implant comprising:
    a clamp assembly comprising:
        a superior jaw;
        an inferior jaw opposedly positioned to the superior
           jaw;
        a clamp body defining a ball joint connecting the
           superior jaw to the inferior jaw,
           wherein the clamp body defines a socket;
    an implant assembly; and
    a connection system comprising:
        a rod having a head and an end;
        a rod screw positioned proximate the head of the rod
           and received within the clamp body;
        a locking screw received within the clamp body,
           wherein the locking screw contacts an outer surface
           of the superior jaw;
clamping a first vertebra between the superior jaw and the
    inferior jaw of the clamp assembly;

wherein clamping the first vertebra comprises rotating
        the locking screw to thereby advance the locking
        screw along an outer surface of the superior jaw;
fastening the implant assembly to a second vertebra;
inserting the head of the rod into the socket;
coupling the end of the rod to the implant assembly to
    connect the clamp assembly with the implant assembly;
    and
rotating the rod screw,
    wherein rotating the rod screw locks the head of the rod
        into the socket to stabilize the spinal implant.

20. The method of claim 19, wherein rotating the rod screw further comprises:

threading the rod screw into a posterior region of the
    socket, such that an end of the rod screw applies
    pressure to the head of the rod to lock the rod into the
    socket to stabilize the spinal implant.

\* \* \* \* \*